US005152296A

United States Patent [19]
Simons

[11] Patent Number: 5,152,296
[45] Date of Patent: Oct. 6, 1992

[54] DUAL-FINGER VITAL SIGNS MONITOR

[75] Inventor: Tad D. Simons, Palo Alto, Calif.

[73] Assignee: Hewlett-Packard Company, Palo Alto, Calif.

[21] Appl. No.: 487,341

[22] Filed: Mar. 1, 1990

[51] Int. Cl.$^5$ .............................................. A61B 5/02
[52] U.S. Cl. ................................... 128/670; 128/633; 128/679; 128/696
[58] Field of Search ............... 128/670, 680, 681, 686, 128/689, 690, 633, 696, 679

[56] References Cited

U.S. PATENT DOCUMENTS

| | | | |
|---|---|---|---|
| 3,858,574 | 1/1975 | Page | 128/205 T |
| 4,183,360 | 1/1980 | Carlson et al. | 128/666 |
| 4,406,289 | 9/1983 | Wesseling et al. | 128/670 |
| 4,432,374 | 2/1984 | Osanai | 128/694 |
| 4,475,554 | 10/1984 | Hyndman | 128/664 |
| 4,539,997 | 9/1985 | Wesseling et al. | 236/667 |
| 4,718,428 | 7/1988 | Russell | 128/679 |
| 4,726,382 | 2/1988 | Boehmer et al. | 128/667 |
| 4,821,734 | 4/1989 | Koshino | 128/680 |
| 4,860,759 | 8/1989 | Kahn et al. | 128/668 |
| 4,883,055 | 11/1989 | Merrick | 128/633 |
| 4,974,607 | 12/1990 | Miwa | 128/904 |
| 5,050,612 | 9/1991 | Matsumura | 128/670 |

FOREIGN PATENT DOCUMENTS

| | | |
|---|---|---|
| 0024772 | 3/1981 | European Pat. Off. . |
| 0104771 | 8/1983 | European Pat. Off. . |
| 81/03606 | 6/1981 | PCT Int'l Appl. . |

OTHER PUBLICATIONS

Yoshiya et al., "Spectrophotometric Monitoring of Arterial Oxygen Saturation in the Fingertip", *Med. & Biol. Eng. & Comput.*, 1980; 18:27-32.

Yamakoshi et al., "New oscillometric method for indirect measurement of systolic and mean arterial pressure in the human finger", *Med. & Biol. Eng. & Comput.*, 1982; 20:314-318.

Mendelson et al., "Spectrophotometric Investigation of Pulsatile Blood Flow for Transcutaneous Reflectance Oximetry", *Adv. Exp. Med. Biol.*, 1981; 159:93-102.

Boehmer, "Continuous, Real-Time, Noninvasive Monitor of Blood Pressure: Penaz Methodology Applied to the Finger", *Journal of Clinical monitoring*, 1987; vol. 3, No. 4, 282-287.

Yoshida et al., "Non-Invasive Spectrophotometric Estimation of Arterial Oxygen Saturation", *Non-Invasive Measurements:* 2 1983; 251-286.

Yamakoshi et al., "Current Developments in non-invasive measurement of arterial blood pressure", *J. Biomed. Eng.*, 1988; vol. 10, 130-137.

(List continues on next page.)

Primary Examiner—William E. Kamm
Assistant Examiner—Kevin Pontius
Attorney, Agent, or Firm—Jack H. Wu

[57] ABSTRACT

A Dual-Finger Vital Signs Monitor is disclosed. The present invention overcomes problems suffered by previous patient monitors by providing a simultaneous and continuous measurement of three primary vital signs: ECG and heart rate, blood pressure, and blood oxygen saturation. The invention employs a pair of finger cuffs that each include an electro-cardiographic electrode, a first LED and detector pair for blood pressure measurement, and a second LED and detector pair for blood oxygenation measurement. The electrodes are connected to a voltmeter which displays an electrocardiogram. The first LED and detector in each cuff function as a finger-photoplethysmographic pressure sensor. A pair of gas lines connect each finger cuff to a pair of pressure controllers, which each include a fluid reservoir. One of the servos is linked to a blood pressure meter. The second LED and detector pair in each cuff are each connected to a pair of oximeters. All the sensors operate independently. The use of two finger cuffs affords substantial advantages for signal processing and data interpretation. The redundancy of sensors greatly reduces the incidence of false warnings. The Dual-Finger Vital Signs Monitor provides a non-invasive and reliable device for monitoring patients who may suffer from cardiac or respiratory difficulties. This invention constitutes a major step forward in the filed of medical instrumentation.

21 Claims, 5 Drawing Sheets

OTHER PUBLICATIONS

Smith et al., "Evaluation of two prototype devices producing noninvasive, pulsatile, calibrated blood pressure measurement from a finger", *J. of Clinical monitoring*, 1985; vol. 1, No. 1, 17–29.

Shimada et al., "Effects of multiple scattering and peripheral circulation on arterial oxygen saturation measured with a pulse-type oximeter", *Med. & Biol. Eng. & Comput.*, 1984; 22:475–478.

Penaz, "Photoelectric measurement of blood pressure, vol. and flow in the finger", *Digest of the 10th Annual Conf. on Med. & Biol. Engineering*, 1973, Dresden, 7-2.

Shimazu et al., "Idea to measure diastolic arterial pressure by volume oscillometric method in human fingers", *Med. & Biol. Eng. & Comput.*, 1986; 24:549–554.

Penaz et al., "Beitrag zu fortlaufenden indirecktn Blutdruckmessung", *Zschr. inn. Med. Jahrg.* 31, 1976; Heft 24,1030–1033.

Yamakoshi et al., "Indirect Measurement of Instantaneous Arterial Blood Pressure in the Human Finger by the Vascular Unloading Technique", *IEEE Transactions on Biomed. Eng.*, vol. BME-278, No. 3, 1980; 150-155.

Molhoek et al., "Evaluation of the Penaz servo-plethysmomanomether for the continuous, non-invasive measurement of finger blood pressure", *Basic Res. Cardiol.*, 1984; 79:598–609.

Sengoku et al., *Japan J. Med. Electron Biol. Eng.*, 1985; 23(6): 410–11.

Advertisement for a continuous NIBP monitor from Ohmeda.

Advertisement for a blood pressure monitor from Critikon.

Advertisement for an oxygen saturation monitor for Spectramed.

Advertisement for an oximeter/capnograph from Criticare Systems.

Advertisement for an oximeter/capnograph from Ohmeda.

Sarnquist et al., "Accuracy of a New Non-Invasive Oxygen Saturation Monitor", *Anesthesiology*, 1980; vol. 53, No. 3; S163.

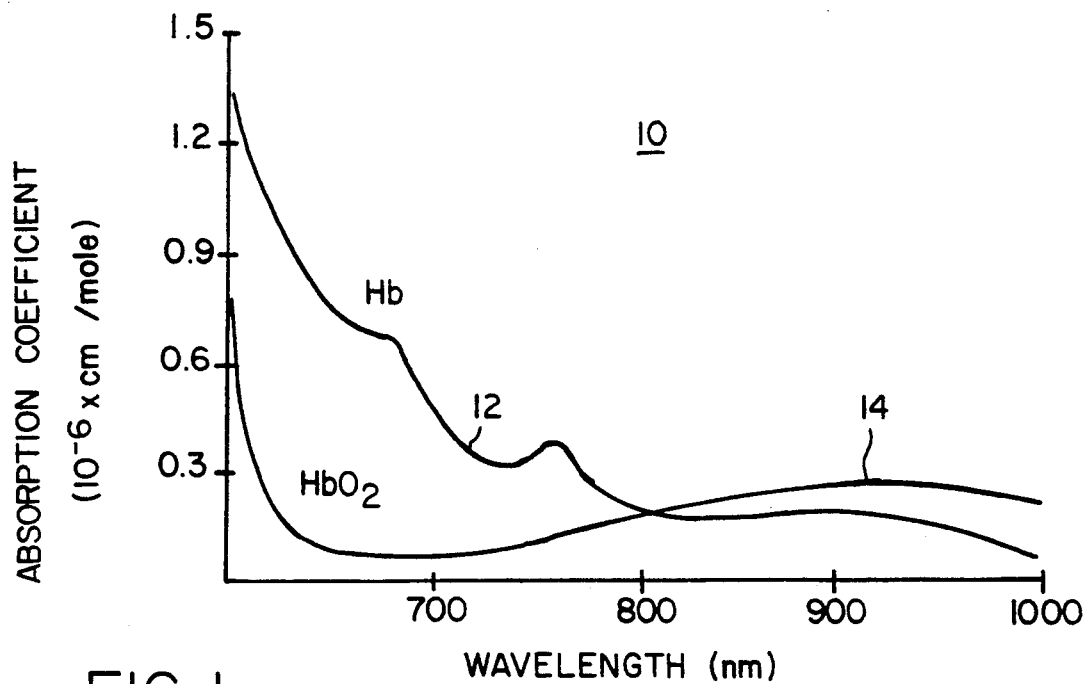
FIG. 1
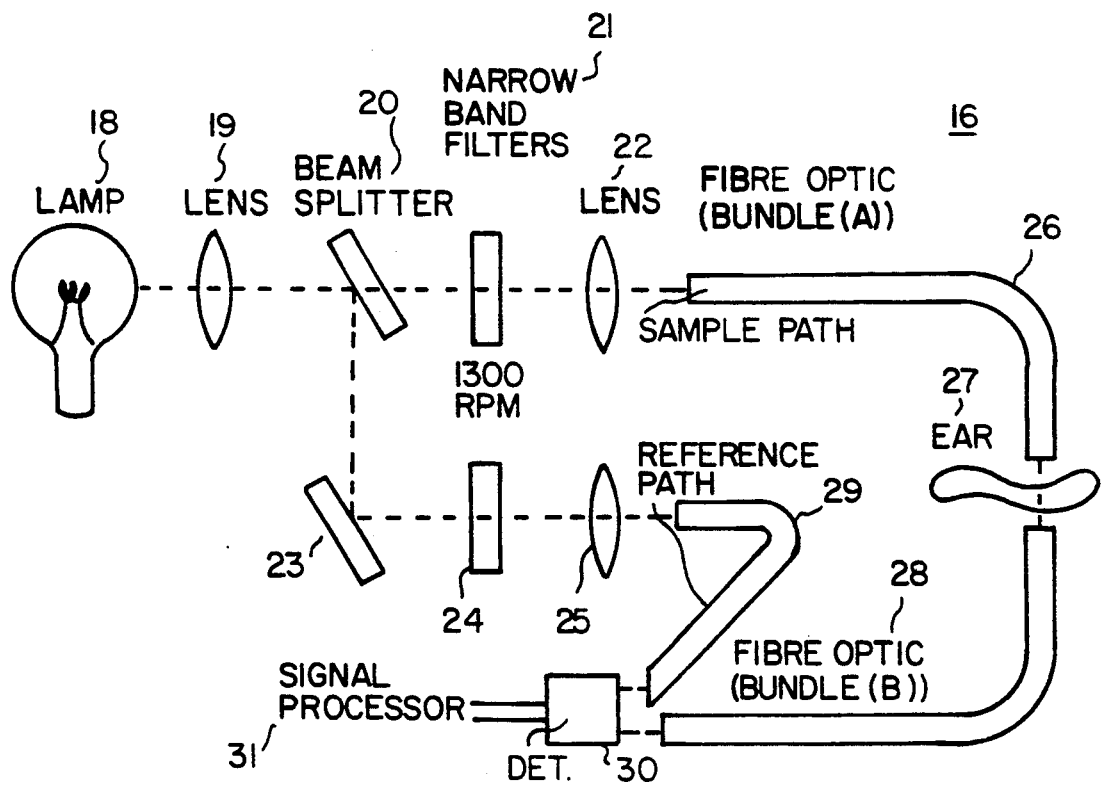
FIG. 2(a)- Prior Art

FIG. 2(b) – Prior Art

DUAL-FINGER VITAL SIGNS MONITOR

BACKGROUND OF THE INVENTION

The present invention is an apparatus that provides a simultaneous measurement of three primary vital signs of a patient. The Dual-Finger Vital Signs Monitor is a convenient, non-invasive, highly accurate, and reliable instrument that can be used to help safeguard the life of a patient who is in grave danger due to potential cardiac and respiratory failure.

Critically ill and seriously injured patients require constant care and attention. Doctors, nurses, and hospital technicians need a continuous flow of information about the many patients under their care. Electrocardiogram (ECG), heart rate, and blood pressure measurements are two primary vital signs that indicate the health of a patient. When these two common indices of wellness fall below normal readings, a patient is usually in distress and requires immediate treatment. Dangerous conditions brought about by a cardio-vascular or pulmonary disease, severe trauma, or drug abuse may bring about a failure of the lungs and heart to supply the bloodstream with life-giving oxygen. Such a potentially fatal deficiency can be detected by continually gauging the amount of hemoglobin in the bloodstream that is carrying oxygen. This third vital sign, which manifests oxygen saturation of the blood, is especially critical because a rapid decline in oxygen in the bloodstream is associated with increased risk of patient mortality.

Many devices that measure these three vital signs separately are currently available to the health-care industry. Several conventional systems employ a single flexible membrane which envelops the finger to measure blood pressure or blood oxygen levels. Information about the heart is supplied by separate wire electrodes and leads that measure voltages on the skin of the patient and that are displayed in a familiar electro-cardiogram (ECG). The ECG is a measurement of the changing potentials generated by the electrical activity of the heart. These previous measurements are inconvenient because they require separate instruments and separate cables which connect to the patient. The motion of the patient can also compromise the readings. If the flexible membrane remains constantly pressurized, this constriction can place great stress on the finger and may, eventually, cause tissue damage. These earlier vital sign meters are also plagued by false readings that can cause confusion in a hospital ward. The frequent incorrect reports of patient distress are often attributable to a reliance upon single sensors, which may warn of dangerous conditions based upon spurious signals generated by the inadvertent and undesirable motion of the patient's finger.

The shortcomings of conventional patient monitoring devices has presented a major challenge to designers in the medical instrumentation field. The development of a reliable and highly accurate vital signs monitor that provides a simultaneous measurement of heart rate, blood pressure, ECG, and blood oxygenation would constitute a major technological advance in the healthcare industry. The enhanced performance that could be achieved using such an innovative device would satisfy a long felt need within the medical profession and would enable hospital equipment manufacturers to help their customers save substantial expenditures of time and money.

SUMMARY OF THE INVENTION

The Dual-Finger Vital Signs Monitor disclosed and claimed in this patient application overcomes the problems suffered by previous patient monitors by providing a simultaneous and continuous measurement of three primary vital signs: ECG and heart rate, blood pressure, and blood oxygen saturation. The present invention employs a pair of finger cuffs that each include an electrocardiographic electrode, a first radiation source and detector pair for blood pressure measurement, and a second radiation source and detector pair for blood oxygenation measurement. The electrodes are connected to a voltmeter which displays an electrocardiogram. The first radiation source and detector pairs in each cuff function as a finger-photoplethysmographic pressure sensor. A pair of fluid conduits connect each finger cuff to a pair of blood pressure controllers, which each include a fluid reservoir. The second radiation source and detector pair in each cuff are each connected to a pair of oximeters. All the sensors operate independently. The use of two finger cuffs affords substantial advantages for signal processing and data interpretation. The redundancy of sensors greatly reduces the incidence of false warnings. The two finger cuffs may be inflated and pressed into service in a regularly alternating sequence, so that the blood flow in the patient's finger is not constricted for a time period that would cause tissue damage.

The Applicant's innovative Dual-Finger Vital Signs Monitor is a reliable, cost-effective, and powerful tool that will enable physicians and nurses to provide higher quality care and to save lives.

An appreciation of other aims and objectives of the present invention and a more complete and comprehensive understanding of this invention may be achieved by studying the following description of a preferred embodiment and by referring to the accompanying drawings.

BRIEF DESCRIPTION OF THE DRAWINGS

FIG. 1 is a graph which compares the absorption coefficients of oxygenated and deoxygenated hemoglobin for various wavelengths of light passed through the bloodstream.

DETAILED DESCRIPTION OF A PREFERRED EMBODIMENT

Previous Methods and Devices

FIG. 1 is a comparison 10 of two curves which reveals absorption coefficients at various wavelengths of incident light for deoxyhemoglobin 12 and oxyhemoglobin 14 in the blood. Persons ordinarily skilled in the art of non-invasive blood measurement techniques have exploited the differences between the absorbance of oxyhemoglobin and deoxyhemoglobin to measure the level oxygen in a patient's bloodstream.

Figure 2:
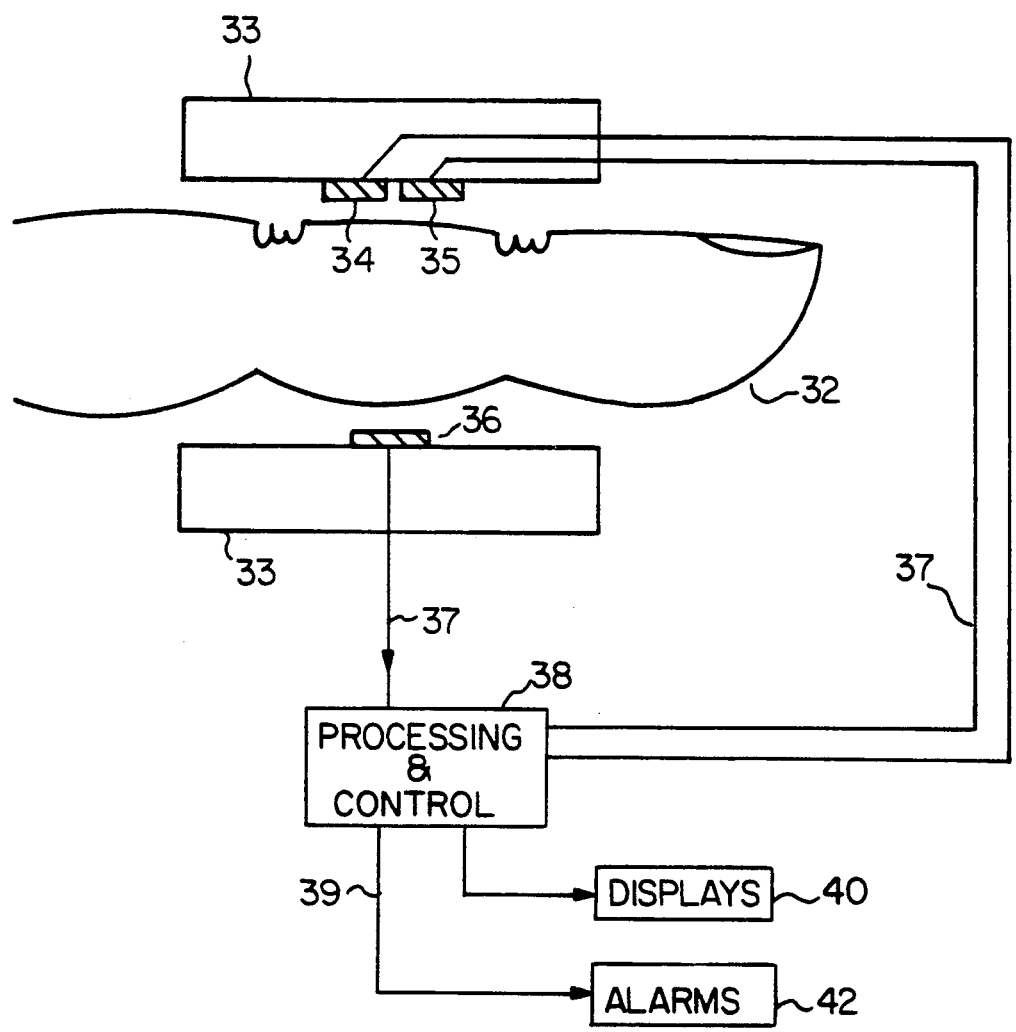
FIG. 2(a) is a schematic depiction of a conventional ear oximeter.
FIG. 2(b) is a schematic illustration of a convention pulse oximeter.

FIG. 2(a) depicts one type of conventional oximeter which is based upon the different reflectivity of oxygen-bearing and deoxygenated hemoglobin. Hewlett-Packard's Multiple-Wavelength Ear Oximeter 16 comprises a light source 18, a lens 19, a beam splitter 20, a narrow band filter wheel 21, a lens 22, a beamsplitter 23, a filter 24, a lens 25, optical fiber bundles 26 and 28 which are placed on either side of a patient's earlobe 27. A reference path 29 conveys light to a detector 30 which is connected to a signal processor 31. Eight filters are arranged on a rotating wheel 21 so that a set of selected wavelengths of light are sequentially directed to the ear 27 through the fiber optic guides. As the filter wheel 21 rotates, a particular wavelength of radiant energy is first focused on the photodetector 30 through the ear 27, and then to the detector 30 via the reference path 29. The ratio of the transmitted light intensity to the incident light intensity is calculated by signal processor 31, which utilizes equations that are well known in the field to determine the oxygen saturation value.

FIG. 2(b) is a schematic illustration of a conventional pulse oximeter. A patient's finger 32 is surrounded by a finger cuff 33 that includes a red LED 34, a near infrared LED 35, and a detector 36. The LEDs 34 and 35 and the detector 36 are coupled by leads 37 to processing and control circuitry 38 which measures blood pressure based upon the amount of red and near infrared radiation sensed by detector 36. Displays 40 and alarms 42 present the blood pressure information to the user.

Figure 3:
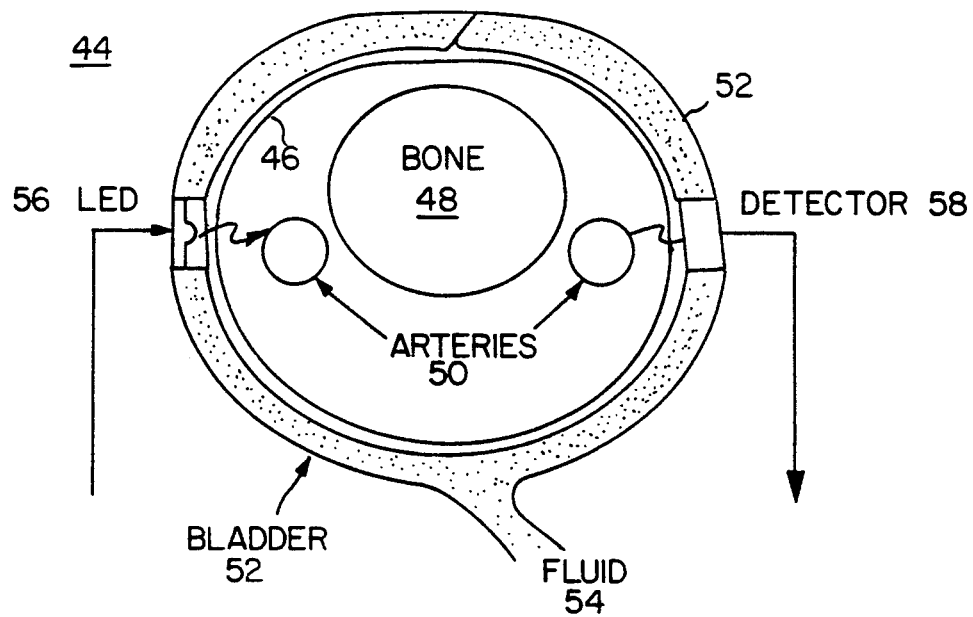
FIG. 3 is a schematic cross-section of a finger surrounded by a blood pressure cuff.

FIG. 3 is a cross-sectional view 44 of a finger surrounded by the cuff of a blood pressure monitor first described by J. Penaz. The epidermis 46, bone 48, and arteries 50 are shown enveloped within a cuff bladder 52 that is pressurized by a fluid supply 54. A light emitting diode 56 and a detector 58 are located on opposite sides of the bladder 52 are employed to infer the volume of the finger arteries 50, which, in turn, provides a measurement for the patient's blood pressure. The technique utilized by the Penaz invention is to measure the size of the artery 50 when the blood pressure within it is the same as the external pressure imposed by the inflatable cuff 52 that has been placed around the finger. The LED 56, detector 58, an pressurized fluid supply 54 are connected to a signal processor (not shown) which computes blood pressure based upon pressure in the cuff bladder 52 while the artery is maintained in an unloaded condition. The systolic, mean, and diastolic pressures can all be determined using this method. The systolic pressure is the blood pressure at ventricular systole, i.e., the end of the heart stroke, and is the highest pressure. Diastolic pressure is the pressure at diastole, when the heart is relaxed, and is the lowest pressure. The mean pressure is the average pressure of the arterial pressure during a complete heart cycle.

Figure 4:
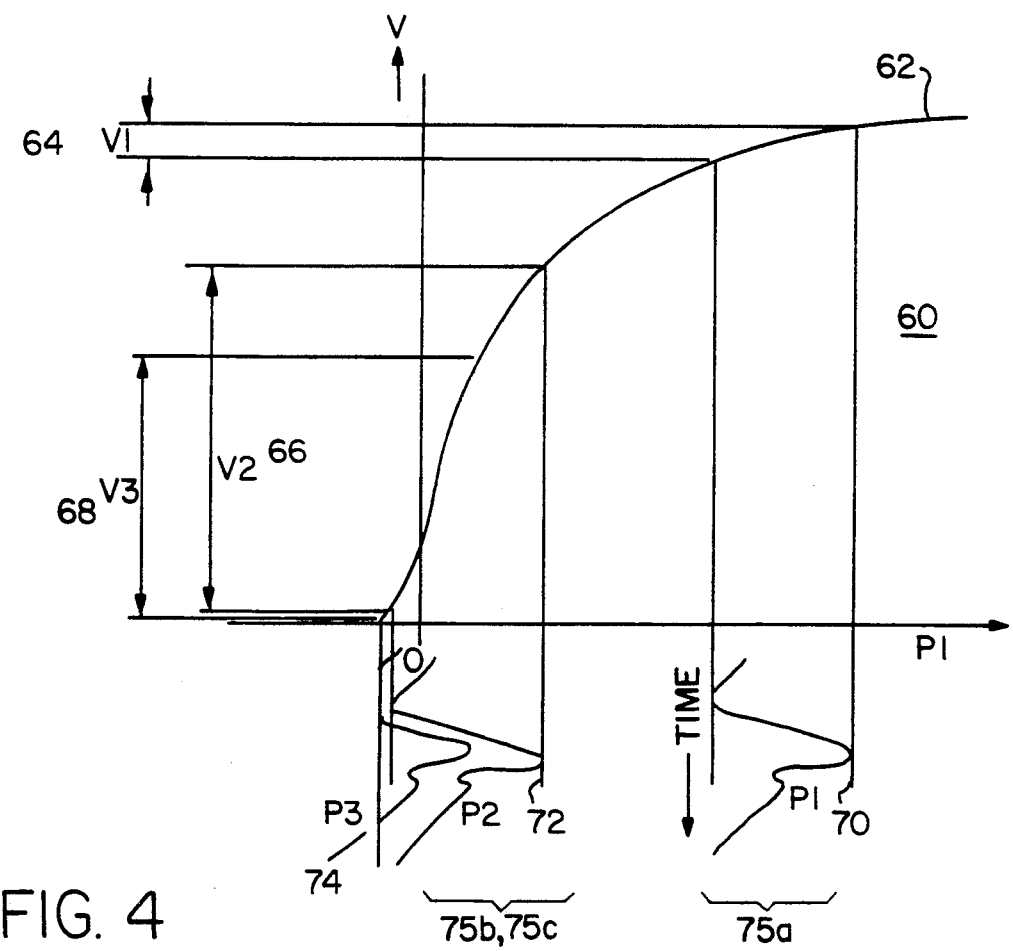
FIG. 4 presents a plot of volume v. pressure for arterial blood in a finger.

FIG. 4 illustrates the pressure v. volume characteristics 60 of a finger artery. Arterial volume is read along the x-axis and the transmural pressure, the difference between the arterial pressure and the finger cuff pressure, is read along the y-axis. Curve 62 represents the dependence of artery size for a given transmural pressure. Volumes 64, 66, and 68 correspond to pressure levels 70, 72, and 74. When the pressure in the cuff surrounding the finger is held constant, the pressure changes are shown by the graphs 75(a,b,c) bounded by pressure levels 70, 72, and 74.

Figure 5:
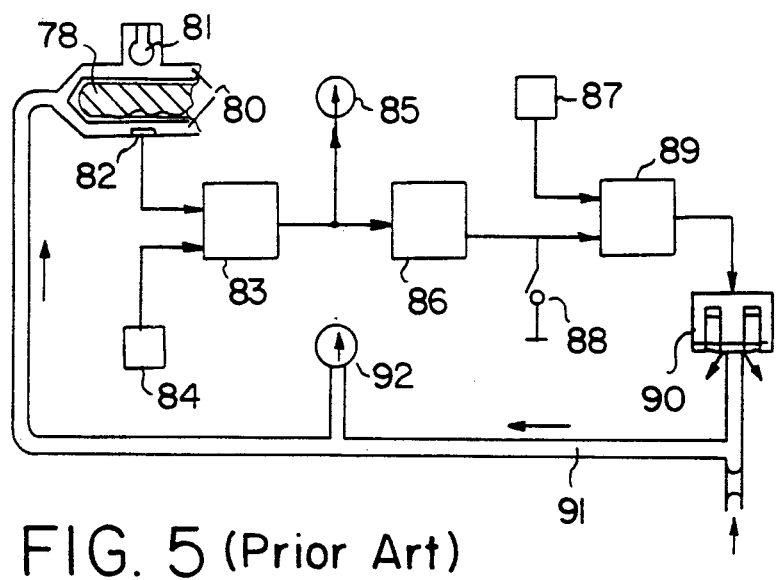
FIG. 5 reveals an illustration of a conventional photoelectric plethysmographic chamber around a patient's finger.

FIG. 5 reveals a schematic diagram showing a patient's finger 78 within a conventional transparent pressure cuff 80 that is commonly used to measure blood pressure. Cuff 80 includes a light source 81 and a photocell 82. The output of the photocell 82 is fed to a difference amplifier 83, which compares the cuff signal with a preselected first external signal input 84. One terminal of a plethysmogram voltmeter 85 is placed between the difference amplifier 83 and a correcting network 86, which is also connected to a switch 88 and a power amplifier 89. A second external signal is 87 is also fed to the power amplifier 89. An electro-pneumatic transducer 90, which is connected to a fluid-filled conduit 91, receives an output signal from the power amplifier.

Figure 6:
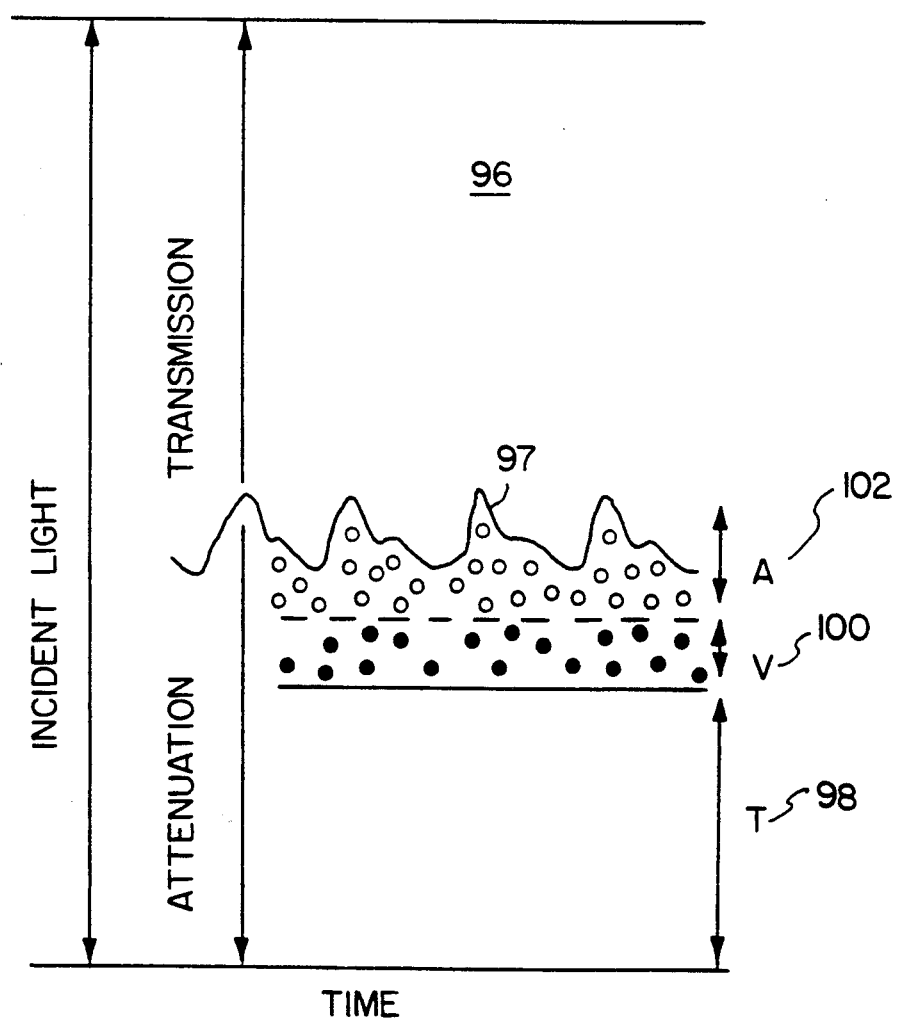
FIG. 6 portrays the attenuation of light passing through a patient's finger. The graph exhibits the separate attenuation components attributable to tissue, venous blood, and arterial blood.

FIG. 6 exhibits a schematic diagram 96 of waveforms generated by the photoelectric output of a pulse oximeter. Curve 97 represents the pulsatile signal from the spectrophotometric analysis of blood flow in the patient's finger. Distances 98, 100, and 102 show the amount of attenuation due to absorption by tissue, venous blood, and arterial blood, respectively. Since the components 98 and 100 are constant, oximetry can be performed using only the fluctuating component attributable to the arterial blood. Beer's Law is employed to calculate the optical density of the light transmitted through the finger. The same methods described above which exploit the different coefficients of absorption for saturated and unsaturated hemoglobin are utilized to determine oxygen levels in the bloodstream.

The Dual-Finger Vital Signs Monitor

Figure 7:
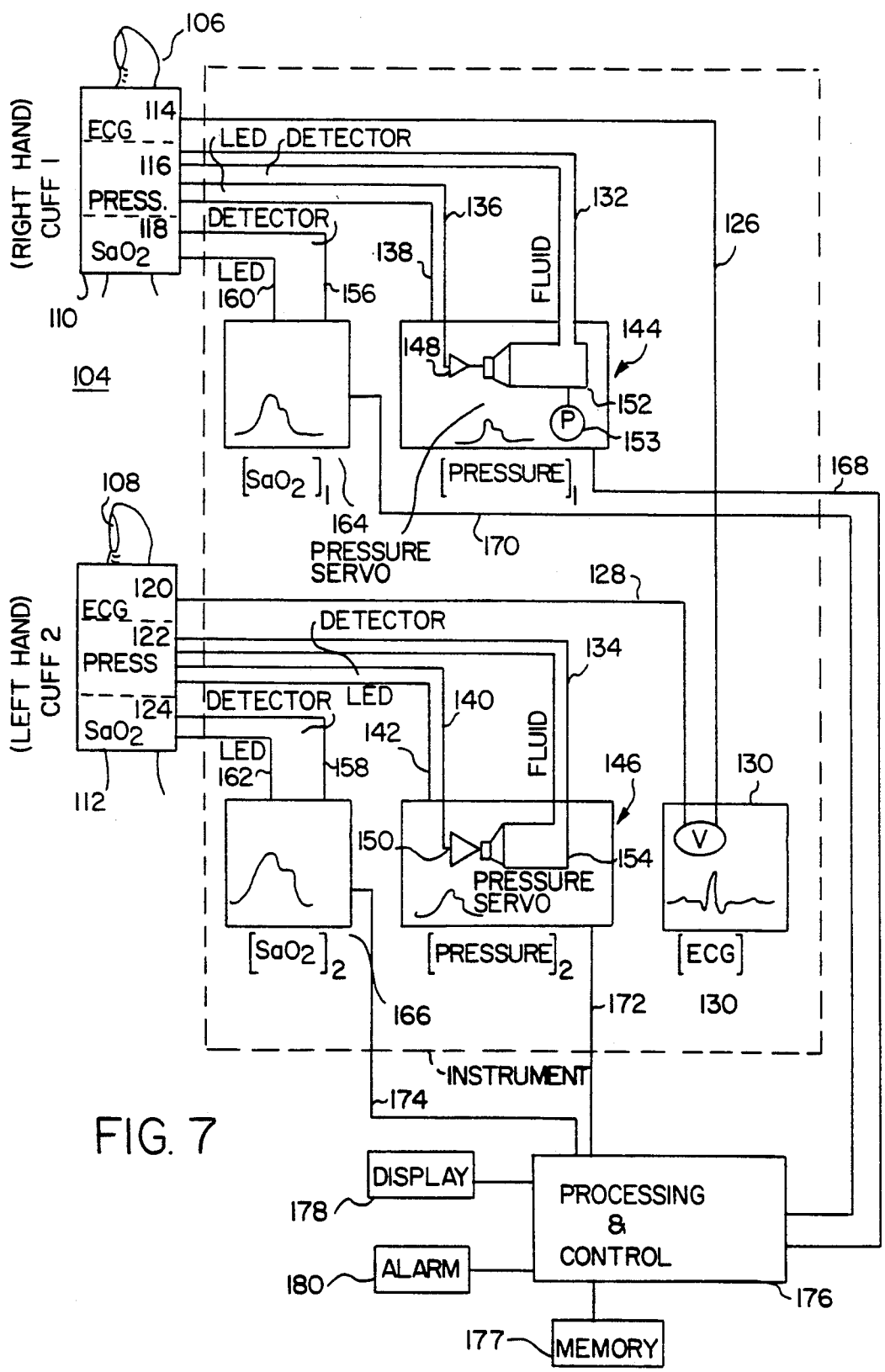
FIG. 7 is a schematic diagram of the present invention, the Dual-Finger Vital Signs Monitor.

FIG. 7 is a block diagram of the present invention, the Dual-Finger Vital Signs Monitor 104. The patient's right and left finger 106 and 108 are surrounded by right and left cuffs 110 and 112. Each cuff includes an ECG transducer portion 114 and 120, a pressure transducer portion 116 and 122, and a hemoglobin oxygenation transducer portion 118 and 124. Leads 126 and 128 from ECG transducers are connected to an ECG analyzer and display 130. A pair of fluid conduits 132 and 134 connect the cuffs 110 and 112 to a pair of pressure controllers 144 and 146. Leads 136 and 140 from the pressure detectors 116 and 122 and leads 138 and 142 from pressure LEDs 116 and 122 are also connected to pressure controllers 144 and 146. Amplifiers 148 and 150 are coupled to pressure servos 152 and 154 which automatically maintain the appropriate fluid level in the cuffs 110 and 112. A blood pressure meter 153 is connected to servo 152. Detector leads 156 and 158 from hemoglobin transducers 118 and 124 as well as LED leads 160 and 162 are connected to an oximeter 164 and 166. Pressure controllers 144 and 146 are connected by leads 168 and 172 to processing and control circuitry 176, which is also coupled to oximeters 164 and 166 by leads 170 and 174. Memory 177, a display 178, and an alarm 180 are also linked to processing and control circuitry 176. The alarm 180 may use a buzzer or horn to provide an audible signal, or may incorporate an LED or lamp that supplies a visual indication.

The present invention is connected to the patient by placing cuffs 110 and 112 over one finger on each hand. This pair of connections is often referred to as a "Lead One" pair, which connotes that this tandem is the first set of electrodes for ECG procedures. This form of coupling is far simpler and more reliable than the many different connections that must be made when several independent conventional instruments are utilized to provide the same measurements. In the preferred embodiment, display 178 provides a digital array which presents heart rate, blood pressure, and blood gas information. All the sensors within the cuffs operate independently. The use of two finger cuffs affords substantial advantages for signal processing and data interpretation. The redundancy of sensors greatly reduces the incidence of false warnings.

The Dual-Finger Vital Signs Monitor provides a non-invasive and reliable device for monitoring patients who may suffer from cardiac or respiratory difficulties. This invention constitutes a major step forward in the field of medical instrumentation.

Although the present invention has been described in detail with reference to a particular preferred embodiment, persons possessing ordinary skill in the art to which this invention pertains will appreciate that various modifications and enhancements may be made without departing from the spirit and scope of the claims that follow.

What is claimed is:

1. A vital signs monitor comprising:
   a transducing means comprising a first transducer means for measuring a plurality of different types of vital signs; said first transducer means comprising a plurality of first detector means each constructed differently from one another for detecting the plurality of different types of vital signs; the plurality of first detector means being mounted proximate one another on a first probe body; said first probe body being capable of being coupled to a patient; and
   a meter means; the meter means providing a measurement of a plurality of test parameters; the meter means being coupled to the plurality of first detector means.

2. A vital signs monitor as in claim 1 further comprising:
   a memory means for storing a plurality of critical vital sign values; said memory means being coupled to the meter means; and
   an alarm means for providing a warning when any one of said plurality of different types of vital signs fall below said plurality of critical vital sign values stored in said memory means; said alarm means being coupled to said memory means.

3. A vital signs monitor as in claim 1 wherein:
   one of the plurality of first detector means mounted on said first probe body is a first hemoglobin oxygenation detector means for sensing a level of hemoglobin saturated with oxygen in said patient;
   the meter means is constructed for providing a measurement of said level of hemoglobin saturated with oxygen;
   said first hemoglobin oxygenation detector means is coupled to said meter means.

4. A vital signs monitor as in claim 1 wherein:
   one of the plurality of first detector means mounted on said first probe body is a first pressure detection means for sensing a blood pressure level in said patient;
   said first probe body comprises a first inflatable pressure cuff means capable of substantially enveloping a first appendage of said patient;
   the meter means is constructed for providing a measurement of said blood pressure level;
   said transducer means further comprises;
   a first fluid conduit means for conveying a fluid to said first inflatable pressure cuff means; said first fluid conduit means being coupled to said first inflatable pressure cuff means and to said first pressure meter means; said first fluid conduit means being for the purposes of inflating the cuff means; and
   a first fluid reservoir means for controlling said fluid in said first fluid conduit means; said first fluid reservoir means being coupled to said meter means.

5. A vital signs monitor as in claim 4 wherein;
   said first inflatable pressure cuff means is a first inflatable finger cuff means; and
   said first appendage of said patient is a first finger digit of said patient.

6. A vital signs monitor comprising:
   a transducing means comprising a first transducer means for measuring a vital sign; said first transducer means comprising a plurality of first detector means mounted proximate one another on a first probe body; said first probe body being capable of being coupled to a patient; and
   a plurality of meter means; each of the meter means providing a measurement of a respective one of a plurality of test parameters; each of the meter means being coupled to a respective one of the first detector means;
   wherein: one of the plurality of first detector means mounted on said first probe body is a first potential difference detection means for sensing an electric field in said patient; and
   one of the plurality of meter means is a voltage meter means for providing a measurement of said electric field; and
   said first potential detection means is coupled to said voltage meter means.

7. A vital signs monitor comprising:
   a transducing means comprising a first transducer means for measuring a vital sign; said first transducer means comprising a plurality of first detector means mounted proximate one another on a first probe body; said first probe body being capable of being coupled to a patient;
   a plurality of meter means; each of the meter means providing a measurement of a respective one of a plurality of test parameters; each of the meter means being coupled to a respective one of the first detector means;
   one of the plurality of first detector means mounted on said first probe body is a first hemoglobin oxygenation detector means for sensing a level of hemoglobin saturated with oxygen in said patient;
   one of the plurality of meter means is a hemoglobin oxygenation meter means for providing a measurement of said level of hemoglobin saturated with oxygen; said hemoglobin oxygenation meter means comprises a first hemoglobin oxygenation meter means;

said first hemoglobin oxygenation detector means is coupled to said first hemoglobin oxygenation meter means;

one of the plurality of first detector means mounted on said first probe body is a first potential difference detection means for sensing an electric field in said patient;

one of the plurality of meter means is a voltage meter means for providing a measurement of said electric field;

said first potential detection means is coupled to said voltage meter means;

one of the plurality of first detector means mounted on said first probe body is a first pressure detection means for sensing a blood pressure level in said patient;

said first probe body comprises a first inflatable pressure cuff means capable of substantially enveloping a first appendage of said patient;

one of the plurality of meter means is a pressure meter means for providing a measurement of said blood pressure level; said pressure meter means comprises a first pressure meter means;

said transducer means further comprises;

a first fluid conduit means for conveying a fluid to said first inflatable pressure cuff means; said first fluid conduit means being coupled to said first inflatable pressure cuff means and to said first pressure meter means; said first fluid conduit means being for the purpose of inflating the first cuff means; and a first fluid reservoir means for controlling said fluid in said first fluid conduit means; said first fluid reservoir means being coupled to said first pressure meter means.

8. A vital signs monitor as in claim 7 wherein;

said first inflatable pressure cuff means is a first inflatable finger cuff means; and said first appendage of said patient is a first finger digit of said patient.

9. A vital signs monitor comprising:

a transducing means comprising;

a first and a second transducer means for measuring a plurality of different types of vital signs; the first transducer means comprising a plurality of first detector means each constructed differently from one another for detecting the plurality of different types of vital signs; the plurality of first detector means being mounted proximate one another on a first probe body; the second transducer means comprising a plurality of second detector means each constructed differently from one another for detecting the plurality of different types of vital signs; the plurality of second detector means being mounted proximate one another on a second probe body; the first and second probe bodies each being capable of being coupled to a patient;

a meter means; the meter means providing a measurement of a plurality of test parameters; being coupled to the plurality of first detector means and to the plurality of second detector means.

10. A vital signs monitor as in claim 9 further comprising:

a memory means for storing a plurality of critical vital sign values; said memory means being coupled to the meter means; and an alarm means for providing a warning when any one of said plurality of different types of vital signs falls below said plurality of critical vital sign values stored in said memory means; said alarm means being coupled to said memory means.

11. A vital signs monitor as in claim 9 wherein:

one of the plurality of first detector means mounted on said first probe body is a first hemoglobin oxygenation detector means for sensing a level of hemoglobin saturated with oxygen in said patient;

one of the plurality of second detector means mounted on said second probe body is a second hemoglobin oxygenation detector means for sensing said level of hemoglobin saturated with oxygen in said patient;

the meter means is constructed for providing a measurement of said level of hemoglobin saturated with oxygen;

the first and second hemoglobin oxygenation detector means each being coupled to the meter means.

12. A vital signs monitor as in claim 9 wherein:

one of the plurality of first detector means mounted on said first probe body is a first pressure detection means for sensing a blood pressure level in said patient;

one of the plurality of second detector means mounted on said second probe body is a second pressure detection means for sensing said blood pressure level in said patient;

said first probe body comprises a first inflatable pressure cuff means capable of substantially enveloping a first appendage of said patient;

said second probe body comprises a second inflatable pressure cuff means capable of substantially enveloping a second appendage of said patient;

the meter means is constructed for providing a measurement of said blood pressure level;

the first and second transducer means further comprise;

a first and a second fluid conduit means for conveying a fluid to the first and second inflatable pressure cuff means; the first and second fluid conduit means each being coupled to a respective one of the first and second inflatable pressure cuff means and to the meter means; the first and second fluid conduit means being for the purpose of each inflating a respective one of the first and second inflatable pressure cuff means; and a first and a second fluid reservoir means for controlling said fluid in the first and second fluid conduit means; the first and second fluid reservoir means each being coupled to the meter means.

13. A vital signs monitor as in claim 12 wherein;

the first and second inflatable pressure cuff means are a first and a second inflatable finger cuff means; and the first and second appendages of said patient are a first and a second finger digit of said patient.

14. A vital signs monitor as in claim 9 wherein the first and second transducer means further comprise a first actuation means for actuating said first probe body and a second actuation means for actuation said second probe body;

said first actuation means being coupled to said first probe body and to said meter means;

said second actuation means being coupled to said second probe body and said meter means;

said first and second actuation means being constructed for respectively actuating said first and second probe bodies in an alternating sequence between two states;

a first state wherein one of said plurality of first detector means senses one of said plurality of different types of vital signs in said patient while said first probe body is actuated and said second probe body is unactuated, and a second state wherein one of said plurality of second detector means senses said one of said plurality of different types of vital signs in said patient while said second probe body is actuated and said first probe body is unactuated.

15. A vital signs monitor as in claim 14 wherein:

one of the plurality of first detector means mounted on said first probe body is a first pressure detection means for sensing a blood pressure level in said patient;

one of the plurality of second detector means mounted on said second probe body is a second pressure detection means for sensing said blood pressure level in said patient;

said first probe body is a first inflatable pressure cuff means capable of substantially enveloping a first appendage of said patient;

said second probe body is a second inflatable pressure cuff means capable of substantially enveloping a second appendage of said patient;

meter means is a first pressure meter means for providing a first measurement of said blood pressure level;

said first actuation means for actuating said first probe body comprises a first fluid conduit and a first fluid reservoir; said second actuation means for actuating said second probe body comprises a second fluid conduit and a second fluid reservoir; the first and second fluid conduit means each being coupled to a respective one of the first and second inflatable pressure cuff means and to the meter means; the first and second fluid reservoir means each being coupled to the meter means for controlling said fluid in the first and second fluid conduit means;

said first and second actuation means being constructed for respectively inflating said first and second pressure cuffs in an alternating sequence between two states; a first state wherein said first pressure detection means senses said blood pressure level in said patient while said first pressure cuff is inflated and said second pressure cuff is deflated, and a second state wherein said second pressure detection means senses said blood pressure level in said patient while said second probe body is inflated and said first probe body is deflated.

16. A vital signs monitor comprising:

a transducing means comprising;

a first and a second transducer means for measuring a vital sign; the first transducer means comprising a plurality of first detector means mounted proximate one another on a first probe body; and the second transducer means comprising a plurality of second detector means mounted proximate one another on a second probe body; the first and second probe bodies each being capable of being coupled to a patient; and a plurality of meter means; each of the meter means providing a measurement of a respective one of a plurality of test parameters; each of the meter means being coupled to a respective one of the first detector means and to a respective one of the second detector means;

wherein: one of the plurality of first detector means mounted on said first probe body is a first potential difference detector means for sensing an electric field in said patient;

one of the plurality of second detector means mounted on said second probe body is a second potential difference detector means for sensing said electric field in said patient; and one of the plurality of meter means is a voltage meter means for providing a measurement of said electric field; the first and second potential difference detector means each being coupled to said voltage meter means.

17. A vital signals monitor as comprising:

a transducing means comprising;

a first and a second transducer means for measuring a vital sign; the first transducer means comprising a plurality of first detector means mounted proximate one another on a first probe body; the second transducer means comprising a plurality of second detector means mounted proximate one another on a second probe body; the first and second probe bodies each being capable of being coupled to a patient;

a plurality of meter means; each of the meter means providing a measurement of a respective one of a plurality of test parameters; each of the meter means being coupled to a respective one of the first detector means and to a respective one of the second detector means;

one of the plurality of first detector means mounted on said first probe body is a first hemoglobin oxygenation detector means for sensing a level of hemoglobin saturated with oxygen in said patient;

one of the plurality of second detector means mounted on said second probe body is a second hemoglobin oxygenation detector means for sensing said level of hemoglobin saturated with oxygen in said patient;

one of the plurality of meter is a hemoglobin oxygenation meter means for providing a measurement of said level of hemoglobin saturated with oxygen; said hemoglobin oxygenation meter means comprises a first and a second hemoglobin oxygenation meter means;

the first and second hemoglobin oxygenation detector means each being coupled to a respective one of the first and second hemoglobin oxygenation meter means;

one of the plurality of first detector means mounted on said first probe body is a first potential difference detector means for sensing an electric field in said patient;

one of the plurality of second detector means mounted on said second probe body is a second potential difference detector means for sensing said electric field in said patient;

one of the plurality of meter means is a voltage meter means for providing a measurement of said electric field;

the first and second potential difference detector means each being coupled to said voltage meter means;

one of the plurality of first detector means mounted on said first probe body is a first pressure detection means for sensing a blood pressure level in said patient;

one of the plurality of second detector means mounted on said second probe body is a second pressure detection means for sensing said blood pressure level in said patient;

said first probe body comprises a first inflatable pressure cuff means capable of substantially enveloping a first appendage of said patient;

said second probe body comprises a second inflatable pressure cuff means capable of substantially enveloping a second appendage of said patient;

one of the plurality of meter means is a pressure meter means for providing a measurement of said blood pressure level; said pressure meter means comprises a first and a second pressure meter means;

the first and second transducer means further comprise;

a first and a second fluid conduit means for conveying a fluid to the first and second inflatable pressure cuff means; the first and second fluid conduit means each being coupled to a respective one of the first and second inflatable pressure cuff means and to a respective one of the first and second pressure meter means; the first and second fluid conduit means being for the purpose of each inflating a respective one of the first and second inflatable pressure cuff means; and a first and a second fluid reservoir means for controlling said fluid in the first and second fluid conduit means; the first and second fluid reservoir means each being coupled to a respective one of the first and second pressure meter means.

18. A vital signs monitor as in claim 17 wherein;
the first and second inflatable pressure cuff means are a first and a second inflatable finger cuff means; and
the first and second appendages of said patient are a first and a second finger digit of said patient.

19. A vital signs monitor as in claim 18 wherein:
the first and second pressure detection means each comprise;
a first light emitting device which each emit radiation through a respective one of the first and second finger digits of said patient;
a first light detector which receives transmitted radiation from said first light emitting device;
the first and second hemoglobin oxygenation detector means each comprise;
a second light emitting device which each emit radiation through a respective one of the first and second finger digits of said patient; and
a second light detector which receives transmitted radiation from said second light emitting device; and
the first and second potential difference detector means each comprise;
an electrode means for obtaining an epidermal voltage.

20. A method for monitoring a vital sign of a patient while reducing resulting tissue damage to said patient, which comprises the steps of:
(a) selecting a first finger digit of said patient;
(b) selecting a second finger digit of said patient;
(c) inserting said first finger digit into a first inflatable finger cuff means on which is mounted a plurality of first detector means, wherein one of the first detector means is a first pressure detection means for sensing a blood pressure level in said patient;
(d) inserting said second finger digit into a second inflatable finger cuff means on which is mounted on a plurality of second detector means, wherein one of the second detector means is a second pressure detection means for sensing said blood pressure level in said patient;
(e) employing said first and second inflatable finger cuff means in an alternating sequence between two states: a first state wherein said first detector means senses said blood pressure level in said first finger digit while said first finger cuff means is inflated and said second finger cuff means is deflated to reduce tissue damage in said patient, and a second state wherein said second detector means senses said blood pressure level in said patient while said second finger cuff means is inflated and said first finger cuff means is deflated to reduce tissue damage in said patient.

21. A method of increasing data integrity in monitoring said vital sign of said patient as in claim 20, wherein:
said first finger digit is selected from one hand of said patient and said second finger digit is selected from an opposing hand of said patient.

* * * * *